(12) United States Patent
Balkovec et al.

(10) Patent No.: US 6,268,338 B1
(45) Date of Patent: Jul. 31, 2001

(54) CYCLOHEXAPEPTIDYL AMINE COMPOUNDS

(75) Inventors: James M. Balkovec, North Plainfield; Frances Aileen Bouffard, Scotch Plains; James F. Dropinski, Piscataway; Robert A. Zambias, Springfield, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/055,996

(22) Filed: Apr. 30, 1993

(51) Int. Cl.$^7$ ............................ A61K 38/00; C07K 38/12

(52) U.S. Cl. ................................. 514/11; 514/9; 514/2; 530/317

(58) Field of Search ................. 514/9, 11, 2; 530/317

(56) References Cited

U.S. PATENT DOCUMENTS

| | | | |
|---|---|---|---|
| 4,173,629 | 11/1979 | Dreyfuss et al. | 514/11 |
| 4,287,120 | 9/1981 | Abbott et al. | 530/317 |
| 4,293,485 | 10/1981 | Debono | 530/317 |
| 4,293,489 | 10/1981 | Debono | 530/317 |
| 4,320,054 | 3/1982 | Abbott et al. | |
| 4,931,352 | 6/1990 | Fromtling et al. | 435/71.3 |
| 4,968,608 | 11/1990 | Giacobbe et al. | 435/71 |
| 5,021,341 | 6/1991 | Giacobbe et al. | 435/71.1 |
| 5,021,403 | 6/1991 | Sesin et al. | 514/9 |
| 5,159,059 * | 10/1992 | Balkovec et al. | 530/317 |

FOREIGN PATENT DOCUMENTS

| | | | |
|---|---|---|---|
| 851310 | 8/1977 | (BE) . | |
| 859067 | 3/1978 | (BE) . | |
| 0 486 011A2 | 5/1992 | (EP) . | |
| 500170 * | 8/1992 | (EP) | 530/317 |

OTHER PUBLICATIONS

W.W. Turner et al., "New Echinocandin Antitungal Agents", American Chemical Society Division of Medicinal Chemistry, 205th ACS National Meeting.
Kim et al, Antimicrobial Agents and Chemotherapy, vol. 31(2), pp. 197–201, (Feb. 1987).*
Cushion et al, Antimicrobial Agents and Chemotherapy, vol. 28(6), pp. 796–801, (Dec. 1985).*

* cited by examiner

*Primary Examiner*—T. D. Wessendorf
(74) *Attorney, Agent, or Firm*—Valerie J. Camara; Mark R. Daniel

(57) ABSTRACT

Cyclohexapeptidyl amine compounds are disclosed of the formula:

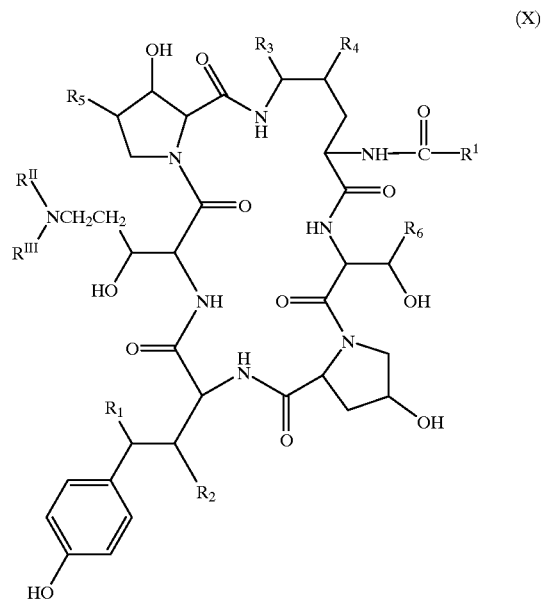

or its acid addition salt,
wherein:
$R_1$ is H or OH;
$R_2$ is H or OH;
$R_3$ is $QC_nH_{2n}NR^V R^{VI}$, $QC_nH_{2n}NR^V R^{VI} R^{VII+} Y^-$, or $Q(CH_2)_{1-3}CR^{VIII} R^{IX} NHR^X$.
$R_4$ is H or OH;
$R_5$ is H, OH or $CH_3$;
$R_6$ is H or $CH_3$;
$R^I$ is

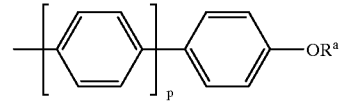

wherein
$R^a$ is $C_1$–$C_{10}$ alkyl; or
$(CH_2)_q NR^b R^c$ wherein $R^b$ and $R^c$ are independently H, $C_1$–$C_{10}$ alkyl or $R^b$ and $R^c$ taken together are

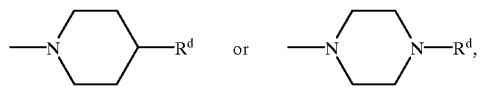

wherein
$R^d$ is $C_1$–$C_{16}$ alkyl, phenyl or benzyl;
$R^{II}$ is H, $C_{1-4}$ alkyl or benzyl;
$R^{III}$ is H, $C_{1-4}$ alkyl or benzyl;
$R^{IV}$ is $R^{II}$ and $R^{III}$ taken together as $-(CH_2)_4-$ or $-(CH_2)_5-$;
$R^V$ is H, $C_1$–$C_4$ alkyl or benzyl;
$R^{VI}$ is H, $C_1$–$C_4$ alkyl or benzyl or $R^V$ and $R^{VI}$ together is $-(CH_2)_4-$ or $-(CH_2)_5-$;
$R^{VII}$ is H or $C_1$–$C_4$ alkyl;
$R^{VIII}$ is H, $(CH_2)_m H$, $(CH_2)_m OH$, $(CH_2)_m NH_2$ or COX wherein
X is $NH_2$, OH or $O(CH_2)_mH$;
$R^{IX}$ is H, $(CH_2)_mH$, or together with $R^{VIII}$ is =O (carbonyl);
$R^X$ is H (except when $R^{VIII}$ and $R^{IX}$ are H, C(=NH)$NH_2$, C(=NH)$CH_2)_{0-3}$H, $CO(CH_2)_{0-3}$H, $CO(CH_2)_mNH_2$, $(CH_2)_{2-4}$OH or $(CH_2)_{2-4}NH_2$;
Q is O or S;
Y is an anion of a pharmaceutically acceptable salt
each m is independently an integer from 1 to 3, inclusive;
n is an integer from 2 to 4, inclusive;
p is an integer from 1 to 2, inclusive and
q is an integer from 2 to 4, inclusive.

9 Claims, No Drawings

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 1:

Xaa Thr Xaa Xaa Xaa Xaa
 1               5

(2) INFORMATION FOR SEQ ID NO: 2:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 2:

Xaa Thr Xaa Xaa Xaa Xaa
 1               5

(2) INFORMATION FOR SEQ ID NO: 3:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 3:

Xaa Ser Xaa Xaa Xaa Xaa
 1               5

(2) INFORMATION FOR SEQ ID NO: 4:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 4:

Xaa Thr Xaa Xaa Xaa Xaa
 1               5

(2) INFORMATION FOR SEQ ID NO: 5:

(i) SEQUENCE CHARACTERISTICS:

(A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 5:

Xaa Thr Xaa Xaa Xaa Xaa
1               5

(2) INFORMATION FOR SEQ ID NO: 6:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 6:

Xaa Thr Xaa Xaa Xaa Xaa
1               5

(2) INFORMATION FOR SEQ ID NO: 7:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 7:

Xaa Ser Xaa Xaa Xaa Xaa
1               5

(2) INFORMATION FOR SEQ ID NO: 8:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 8:

Xaa Thr Xaa Xaa Xaa Xaa
1               5

(2) INFORMATION FOR SEQ ID NO: 9:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 9:

Xaa Thr Xaa Xaa Xaa Xaa

```
1               5
```

(2) INFORMATION FOR SEQ ID NO: 10:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 10:

```
Xaa Ser Xaa Xaa Xaa Xaa
1               5
```

(2) INFORMATION FOR SEQ ID NO: 11:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 11:

```
Xaa Ser Xaa Xaa Xaa Xaa
1               5
```

(2) INFORMATION FOR SEQ ID NO: 12:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 12:

```
Xaa Thr Xaa Xaa Xaa Xaa
1               5
```

(2) INFORMATION FOR SEQ ID NO: 13:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 13:

```
Xaa Thr Xaa Xaa Xaa Xaa
1               5
```

(2) INFORMATION FOR SEQ ID NO: 14:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
            (A) DESCRIPTION: PEPTIDE (xi) SEQUENCE DESCRIPTION: SEQ ID NO: 14:

Xaa Ser Xaa Xaa Xaa Xaa
 1               5

(2) INFORMATION FOR SEQ ID NO: 15:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 15:

Xaa Thr Xaa Xaa Xaa Xaa
 1               5

(2) INFORMATION FOR SEQ ID NO: 16:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 16:

Xaa Thr Xaa Xaa Xaa Xaa
 1               5

(2) INFORMATION FOR SEQ ID NO: 17:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 17:

Xaa Ser Xaa Xaa Xaa Xaa
 1               5

(2) INFORMATION FOR SEQ ID NO: 18:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 18:

Xaa Thr Xaa Xaa Xaa Xaa
 1               5

(2) INFORMATION FOR SEQ ID NO: 19:

```
        (i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 19:

Xaa Thr Xaa Xaa Xaa Xaa
 1                   5

(2) INFORMATION FOR SEQ ID NO: 20:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 20:

Xaa Thr Xaa Xaa Xaa Xaa
 1                   5

(2) INFORMATION FOR SEQ ID NO: 21:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 21:

Xaa Ser Xaa Xaa Xaa Xaa
 1                   5

(2) INFORMATION FOR SEQ ID NO: 22:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 22:

Xaa Thr Xaa Xaa Xaa Xaa
 1                   5

(2) INFORMATION FOR SEQ ID NO: 23:

(i) SEQUENCE CHARACTERISTICS:
            (A) LENGTH: 6
            (B) TYPE: AMINO ACID
            (C) STRANDEDNESS: Not Relevant
            (D) TOPOLOGY: CIRCULAR (ii) MOLECULE TYPE:
            (A) DESCRIPTION: PEPTIDE (xi) SEQUENCE DESCRIPTION: SEQ ID NO: 23:
```

```
Xaa Thr Xaa Xaa Xaa Xaa
1               5

(2) INFORMATION FOR SEQ ID NO: 24:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 24:

Xaa Ser Xaa Xaa Xaa Xaa
1               5

(2) INFORMATION FOR SEQ ID NO: 25:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 25:

Xaa Thr Xaa Xaa Xaa Xaa
1               5

(2) INFORMATION FOR SEQ ID NO: 26:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 26:

Xaa Thr Xaa Xaa Xaa Xaa
1               5

(2) INFORMATION FOR SEQ ID NO: 27:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR (ii) MOLECULE TYPE:
        (A) DESCRIPTION: PEPTIDE (xi) SEQUENCE DESCRIPTION: SEQ ID NO: 27:

Xaa Thr Xaa Xaa Xaa Xaa
1               5

(2) INFORMATION FOR SEQ ID NO: 28:

(i) SEQUENCE CHARACTERISTICS:
        (A) LENGTH: 6
        (B) TYPE: AMINO ACID
        (C) STRANDEDNESS: Not Relevant
        (D) TOPOLOGY: CIRCULAR
```

```
        (ii) MOLECULE TYPE:
             (A) DESCRIPTION: PEPTIDE (xi) SEQUENCE DESCRIPTION: SEQ ID NO: 28:

Xaa Ser Xaa Xaa Xaa Xaa
  1                5

(2) INFORMATION FOR SEQ ID NO: 29:

(i) SEQUENCE CHARACTERISTICS:
             (A) LENGTH: 6
             (B) TYPE: AMINO ACID
             (C) STRANDEDNESS: Not Relevant
             (D) TOPOLOGY: CIRCULAR (ii) MOLECULE TYPE:
             (A) DESCRIPTION: PEPTIDE (xi) SEQUENCE DESCRIPTION: SEQ ID NO: 29:

Xaa Thr Xaa Xaa Xaa Xaa
  1                5
```

CYCLOHEXAPEPTIDYL AMINE COMPOUNDS

The present invention is directed to certain cyclohexapeptidyl amine compounds and to a process for their preparation.

The cyclohexapeptidyl amine compounds of the present invention, Compound X (SEQ ID NOS 1–7, 29) have one amine group directly on the ring and the second amine group as a substituent on the ether group, and may be represented by the formula

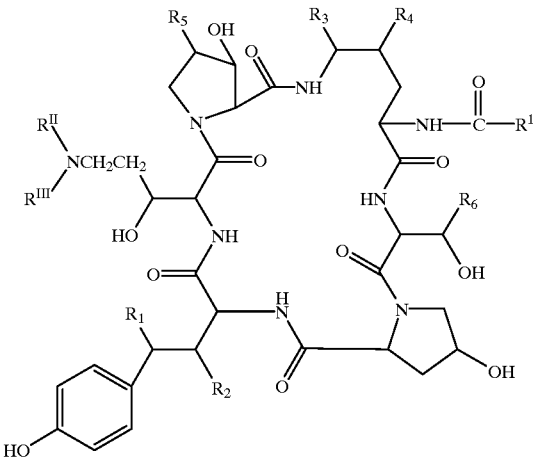

(X)

or its acid addition salt.

In the foregoing and succeeding formulas, $R_1$ is H or OH;
$R_2$ is H or OH;
$R_3$ is $QC_nH_{2n}NR^VR^{VI}$, $QC_nH_{2n}NR^VR^{VI}R^{VII+}Y^-$, or $Q(CH^2)_{1-3}CR^{VIII}R^{IX}NHR^X$
$R_4$ is H or OH;
$R_5$ is H, OH or $CH_3$;
$R_6$ is H or $CH_3$;
$R^I$ is

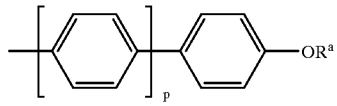

wherein
$R_a$ is $C_1$–$C_{10}$ alkyl; or
$(CH_2)_qNR^bR^c$ wherein $R^b$ and $R^c$ are independently H, $C_1$–$C_{10}$ alkyl or $R^b$ and $R^c$ taken together are

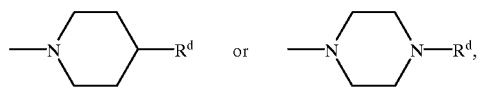

wherein
$R^d$ is $C_1$–$C_{16}$ alkyl, phenyl or benzyl
$R^{II}$ is H, $C_1$–$C_4$ alkyl or benzyl,
$R^{III}$ is H, $C_1$–$C_4$ alkyl or benzyl
$R^{IV}$ is $R^{II}$ and $R^{III}$ taken together as —$(CH_2)_4$— or —$(CH_2)_5$—

$R^V$ is H, $C_1$–$C_4$ alkyl or benzyl
$R^{VI}$ is H, $C_1$–$C_4$ alkyl or benzyl or $R^V$ and $R^{VI}$ together is —$(CH_2)_4$— or —$(CH_2)_5$—
$R^{VII}$ is H or $C_1$–$C_4$ alkyl
$R^{VIII}$ is H, $(CH_2)_mH$, $(CH_2)_mOH$, $(CH_2)_mNH_2$ or COX wherein X is $NH_2$, OH or $O(CH_2)_mH$
$R^{IX}$ is H, $(CH_2)_mH$, or together with $R^{VIII}$ is =O (carbonyl);
$R^X$ is H (except when $R^{VIII}$ and $R^{IX}$ are H), C(=NH)$NH_2$, C(=NH)(CH_2)_{0-3}H$, CO$(CH_2)_{0-3}H$, CO$(CH_2)_mNH_2$, $(CH_2)_{2-4}OH$ or $(CH_2)_{2-4}NH_2$.

Q is O or S;

Y is an anion of a pharmaceutically acceptable salt each m is independently an integer from 1 to 3, inclusive, and n is an integer from 2 to 4, inclusive;

p is an integer from 1 to 2, inclusive and q is an integer from 2 to 4, inclusive.

Hereinafter, when the expression "amine compound" or "Compound X" is employed, it is intended to embrace the amine of formula (X), its acid addition salt or salts. It is to be noted that in Compound X, $R_3$ may be either an amino alkyl ether or a quaternary ammonium alkyl ether. Thus, the amine compound may be an uncharged compound having two amino groups or it may be a mono ammonium compound. When the "amine compound" is an amine, as above defined (Compound X) and $R_3$ is $QC_nH_{2n}NR^VR^{VI}$ or $Q(CH_2)_{1-3}CR^{VIII}R^{IX}NHR^X$, the ultimate compound is uncharged and may be referred to generically as Compound X-a. Compound X-a (Seq. ID No. 1–7, 29) may be represented by the following formula:

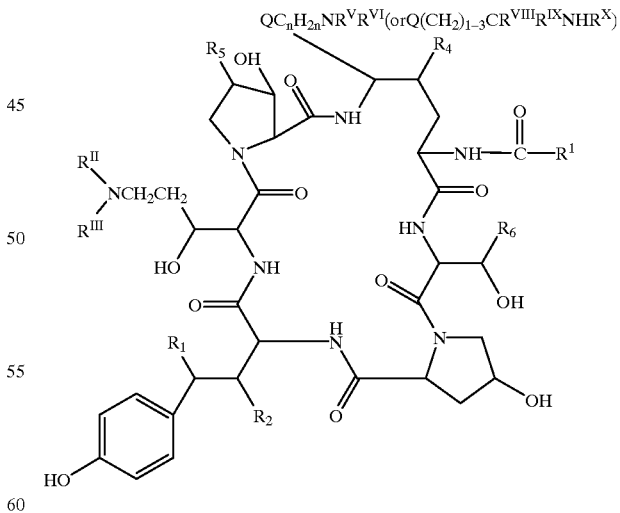

(X-a)

When in the "amine compound" $R_3$ is $QC_nH_{2n}NR^VR^{VI}R^{VII+}Y^-$, the charged portion of the molecule will reside in the amino ether portion and the compound may be referred to as Compound X-b (Seq. ID No. 1–7, 29). Compound X-b may be represented by the following formula:

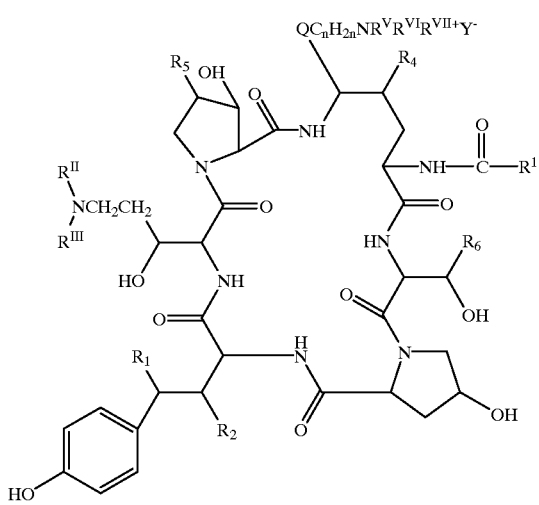

(X-b)

Where the expression "alkyl", "alkenyl" or "alkoxy" is employed, it is intended to include branched as well as straight chain radicals. It is also intended to include an alkyl chain having a cycloalkyl substituent.

Where the expression "ether" is employed, it is intended to include thioethers as will be evident from the context.

Pharmaceutically acceptable salts suitable as acid addition salts as well as salts providing the anion of the quaternary salt are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in Journal of Pharmaceutical Science, 66, 2 (1977).

Representative nuclei for Compound X and the sequence IDs for these compounds may be seen in the following table. Since the peptide nuclei would be the same irrespective of substituents $R^I$, $R^{II}$, $R^{III}$, or $R^{IV}$ and since the sequence identification number is assigned for the nuclear variations, the amines and ammonium salts have the same sequence ID's. Also, since the nucleus amino acid would be the same irrespective of the particular amino alkyl ether, i.e., irrespective of $R^V$, $R^{VI}$ or $R^{VII}$, $R_3$ is considered to be the same for purposes of sequence identification and is not on the table. Further, since the amino acid is not varied irrespective of the change in the lipophilic side chain, separate sequence numbers are not assigned merely on the basis of a different side chain. "Lipophilic side chain" as herein employed refers to $R^I$.

| AMINE COMPOUND NUCLEI | $R_1$ | $R_2$ | $R_4$ | $R_5$ | $R_6$ | SEQ. ID |
|---|---|---|---|---|---|---|
| X-1 | OH | OH | OH | H | $CH_3$ | 1 |
| X-2 | OH | OH | OH | $CH_3$ | $CH_3$ | 2 |
| X-3 | H | OH | OH | $CH_3$ | H | 3 |
| X-4 | OH | H | OH | $CH_3$ | $CH_3$ | 4 |
| X-5 | H | H | H | $CH_3$ | $CH_3$ | 5 |
| X-6 | OH | OH | OH | OH | $CH_3$ | 6 |
| X-7 | H | OH | OH | H | H | 7 |
| X-8 | H | OH | OH | H | $CH_3$ | 29 |

When the compounds are free amines, they are soluble in lower alcohols and polar aprotic solvents such as dimethylformamide (DMF) and pyridine. They are insoluble in solvents such as ether and acetonitrile. When the compounds are quaternary ammonium salts or protonated amines, they are soluble in water and polar solvents.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans, C. tropicalis* and *C. pseudotropicalis*, and Aspergillus species such as *A. fumigatus, A. flavus* and *A. niger*. They are also useful for the treatment and/or prevention of *Pneumocystis carinii* pneumonia to which immune compromised patients are especially susceptible as hereinafter described.

The previously noted solubility properties are advantageous for utilization in therapeutic applications, especially in injectable compositions.

The compounds of the present invention may be obtained from derivatives of natural products through a sequence of reactions seen in the accompanying flow diagram.

The starting material represented by formula (E), which is generally a side chain derivative of a natural product and which may be obtained as hereinafter described, is first subjected to dehydration (Step A) to produce a nitrile of formula (F) which is then reduced (Step B) to an amine G ($R^{II}$, $R^{III}$ are H). which if a substituted amine is desired, may be alkylated by reductive alkylation with an appropriate aldehyde and a reducing agent such as sodium cyanoborohydride to obtain Compound G ($R^{II}$ and $R^{III}$ are alkyl or benzyl).

When Compound G has a nuclear configuration which is different from that obtained from a natural product, it may be obtained by reduction of an OH.

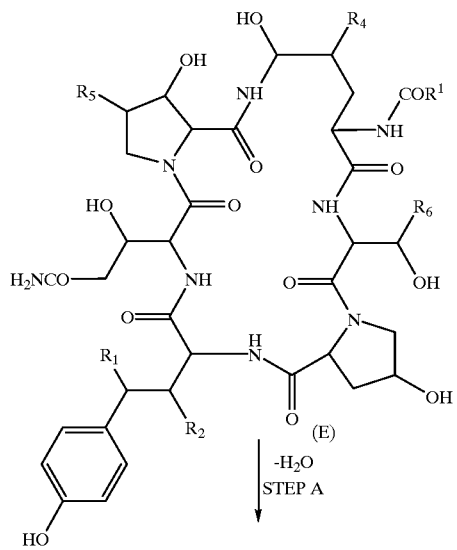

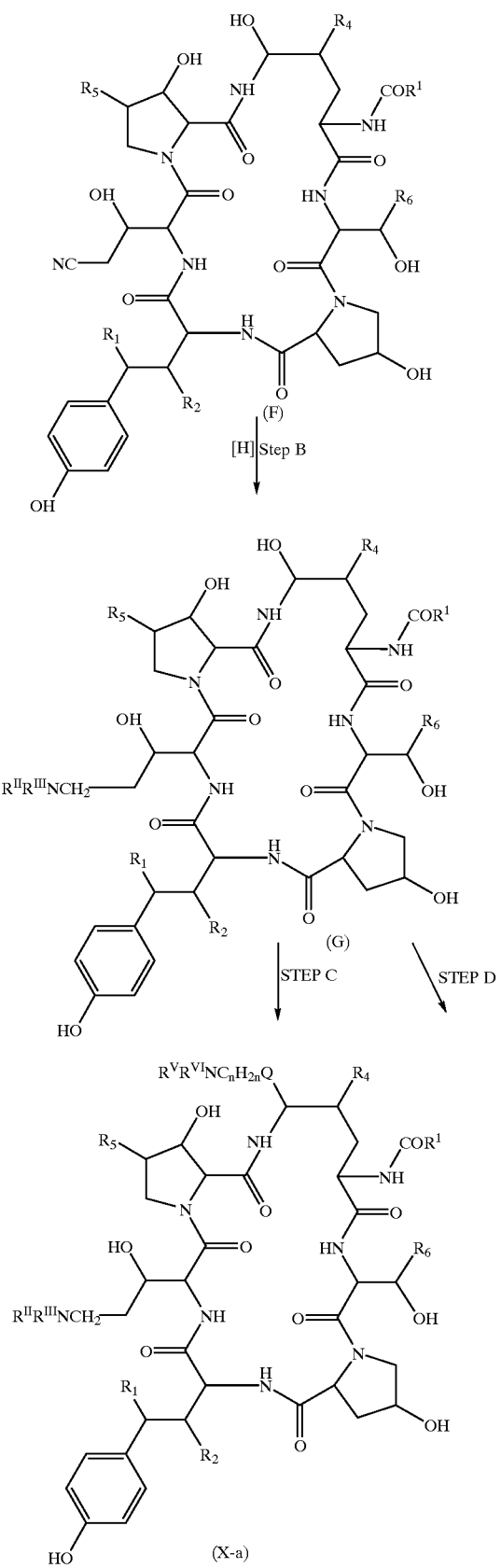

(F)

[H] Step B (G)

STEP C    STEP D (X-a)

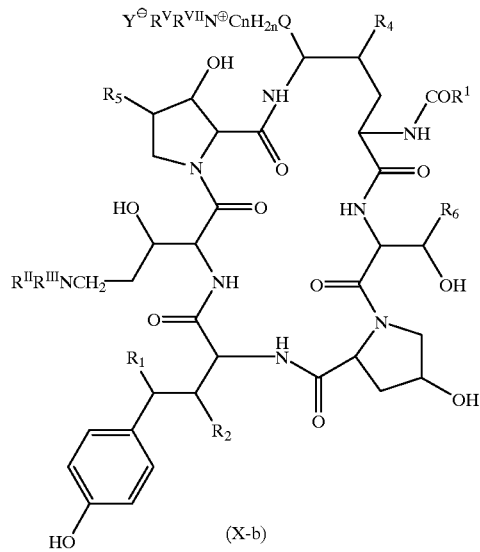

(X-b)

Compound G is representative novel compound which is claimed in concurrently filed copending application in the name of James M. Balkovec, Milton L. Hammond and Robert A. Zambias Ser. No. 07/058,657.

Compound G may be converted to the aminoalkyl ether by adding 1 to 10 equivalents of strong organic or mineral acid such as camphorsulfonic acid or hydrochloric acid to a solution of cyclohexapeptidyl propanolamine (Compound G) and 20 to 200 equivalents of the appropriate amino alcohol or aminothiol in the form of an acid addition salt, such as the hydrochloride or hydrobromide, in an appropriate solvent such as dimethyl sulfoxide (DMSO) or dimethylformamide (DMF) and the mixture stirred at room temperature for one to seven days. The reaction is monitored by HPLC and when determined to be complete, the reaction mixture is diluted with 5 to 50 volumes of water and the entire mixture applied to reverse phase chromatography column. "LICHROPREP" C-18 (E. Merck) column is representative of an appropriate column. The column is then eluted with a weakly eluting solvent such as 5 percent acetonitrile in water (containing 0.1 percent trifluoroacetic acid (TFA) or acetic acid) to remove excess amino-alcohol or aminothiol, then with a stronger eluting solvent such as 10 to 50 percent acetonitrile to elute the product. Fractions containing the desired amine compound may be combined and concentrated to isolate the acid addition salt, Compound X-a, according to Step D.

Compound G may be converted to Compound X-b in a similar manner by adding 1–10 equivalents of a strong organic or mineral acid to a stirred solution of cyclohexapeptidyl propanolamine and 20 to 200 equivalents of the appropriate alkylammonium alcohol or thiol in an appropriate solvent such as DMSO or DMF, and the mixture stirred at room temperature for one to seven days until substantial completion of the reaction as can be determined by HPLC. The reaction mixture is then diluted with 5 to 50 volumes of water and the entire mixture applied to a reverse phase chromatography column. The column then may be eluted with a weakly eluting solvent such as 5 percent acetonitrile to remove excess amino alcohol or thiol and then with 10 to 50 percent acetonitrile to elute the product X-b.

As can be seen from the foregoing flow diagram, the amino acids in the nucleus remain the same except at the hydroxyglutamine. The aminoalkyl ethers are derivatives which do not change the nature of the amino acids. The sequence identification of the amines or ammonium compounds (at the original hydroxyglutamine) from which the aminoalkyl ethers or tinoethers are made would be the same since the amine and hydroxy group of the amino acid remain unchanged. The sequence identification of the starting material and nitrile intermediate are given below.

The sequence identification of the starting materials for the dehydration step are:

| STARTING MATERIAL (E) | $R_1$ | $R_2$ | $R_4$ | $R_5$ | $R_6$ | Seq. ID |
|---|---|---|---|---|---|---|
| E-1 | OH | OH | OH | H | $CH_3$ | 8 |
| E-2 | OH | OH | OH | $CH_3$ | $CH_3$ | 9 |
| E-3 | H | OH | OH | $CH_3$ | H | 10 |
| E-4 | OH | H | OH | $CH_3$ | $CH_3$ | 11 |
| E-5 | H | H | H | $CH_3$ | $CH_3$ | 12 |
| E-6 | OH | OH | OH | OH | $CH_3$ | 13 |
| E-7 | H | OH | OH | H | H | 14 |

The sequence identification of the nitriles are:

| NITRILE COMPOUND (F) | $R_1$ | $R_2$ | $R_4$ | $R_5$ | $R_6$ | Seq. ID |
|---|---|---|---|---|---|---|
| F-1 | OH | OH | OH | H | $CH_3$ | 15 |
| F-2 | OH | OH | OH | $CH_3$ | $CH_3$ | 16 |
| F-3 | H | OH | OH | $CH_3$ | H | 17 |
| F-4 | OH | H | OH | $CH_3$ | $CH_3$ | 18 |
| F-5 | H | H | H | $CH_3$ | $CH_3$ | 19 |
| F-6 | OH | OH | OH | OH | $CH_3$ | 20 |
| F-7 | H | OH | OH | H | H | 21 |

The sequence identification of the propanolamines are:

| PROPANOLAMINE COMPOUND | $R_1$ | $R_2$ | $R_4$ | $R_5$ | $R_6$ | Seq. ID |
|---|---|---|---|---|---|---|
| G-1 | OH | OH | OH | H | $CH_3$ | 22 |
| G-2 | OH | OH | OH | $CH_3$ | $CH_3$ | 23 |
| G-3 | H | OH | OH | $CH_3$ | H | 24 |
| G-4 | OH | H | OH | $CH_3$ | $CH_3$ | 25 |
| G-5 | H | H | H | $CH_3$ | $CH_3$ | 26 |
| G-6 | OH | OH | OH | OH | $CH_3$ | 27 |
| G-7 | H | OH | OH | H | H | 28 |

The first step in the preparation of Compound X (Seq. ID Nos. 1–7, 29) is the dehydration of the carboxamide group of Compound E to the nitrile of Compound F. The reaction is preferably carried out under nitrogen with cyanuric chloride in a solvent in the presence or absence of molecular sieves.

Suitable reagents which may be employed in place of cyanuric chloride are anhydrides such as acetic anhydride, trifluoroacetic anhydride and phosphorus pentoxide; acid chlorides such as oxalyl chloride, phosphorus oxychloride, thionyl chloride, p-toluenesulfonyl chloride and chlorosulfonyl isocyanate; phosphonium reagents such as phosphorus pentachloride, triphenylphosphine/carbon tetrachloride, triphenylphosphonium ditriflate and triphenylphosphonium dichloride; carbodiimides such as dicyclohexylcarbodiimide; other dehydrating agents such as aluminum chloride, titanium tetrachloride, ethyl(carboxysulfamoyl) triethylammonium hydroxide inner salt.

Suitable solvents include dimethylformamide or weakly basic solvents such as pyridine, collidine and the like.

Molecular sieves may be in the size range 3A to 5A.

The relative amounts of Compound E (Seq. ID Nos. 8–14) and reagents vary, but in general the dehydrating agent is used in excess. From about 1.5 to 15 equivalents of the dehydrating agent are employed. When employed the molecular sieves are used in amounts of at least tenfold by weight.

In carrying out the reaction, a suspension of molecular sieves in a rigorously dried solvent is first prepared, and while stirring under an atmosphere of nitrogen, there is added, cyanuric chloride or other dehydrating agent and thoroughly mixed. To the resulting mixture while stirring under an atmosphere of nitrogen is added the starting material, Compound E and the stirring continued for about 12 to 24 hours or until HPLC analysis of the reaction mixture indicates substantial completion of the reaction with the formation of the nitrile. When the HPLC analysis shows substantial completion of the reaction, the sieves are removed by filtration, preferably on a sintered glass funnel, and the filtrate concentrated and purified by preparative HPLC. The mobile phase used in the purification are varying ratios of a water/acetonitrile composition and an acetonitrile/water composition. These compositions are referred to as A and B. Composition A is 95/5 water/acetonitrile containing 0.1% trifluoroacetic acid (TFA) or acetic acid. Composition B is 95/5 acetonitrile/water containing 0.1% TFA or acetic acid. The exact mobile phase used for HPLC assays and the mobile phase used in preparative HPLCs may differ not only from each other but also from compound to compound, but can be determined by the skilled artisan without difficulty.

In carrying out the reaction in the absence of sieves, solid cyanuric chloride is added in a single portion to a solution of Compound E in an aprotic solvent and stirred rapidly for a short time and the reaction mixture then quenched by adding aqueous sodium acetate directly to the reaction mixture. The volatiles are then removed in vacuo to obtain a solid residue which may be purified as above described.

The reduction of the nitrile to the amine may be carried out employing either chemical or catalytic reduction. Sodium borohydride with cobaltous chloride in alcoholic solvent has been found to be particularly useful. When this combination of reagents is used, from about 5 to 50 molar equivalent of sodium borohydride and from 2 to 10 molar equivalents of cobaltous chloride are used for each molar amount of the nitrile.

Other hydride reducing agents such as sodium cyanoborohydride, aluminum hydride, diborane, diisobutyl aluminum hydride and the like also may be used. Frequently these reducing agents are used in combination with a Lewis acid such as cobaltous chloride or aluminum chloride as in the present combination of sodium borobydride and cobaltous chloride.

Catalytic hydrogenation also may be carried out over a variety of catalysts including palladium on carbon, platinum oxide, or rhodium on alumina.

Typical solvents depending on the reagent include alcohols, especially methanol and ethanol, dimethylformamide, pyridine, tetrahydrofuran or other ethers.

When the reduction of the nitrile to the amine is carried out using the preferred chemical procedure, the reaction may be carried out by adding the chemical reducing agent to the nitrile in an alcoholic solution under an atmosphere of nitrogen, and stirring until HPLC analysis using detection by ultraviolet absorption at 210 nm shows substantial completion of the reaction. When sodium borohydride is used in combination with cobaltous chloride, cobaltous chloride is added while stirring to a solution in methanol, or other solvent, of the nitrile, prepared as above described, at ambient temperature, followed by portionwise addition of the sodium borohydride which is accompanied by gas evolution. Stirring is continued for from 12 to 24 hours. The mixture may be quenched with acetic or hydrochloric acid at this time. Then the mixture is diluted with a highly aqueous mobile phase, 70/30 to 50/50 A:B, may be acidified with acetic acid or hydrochloric acid, filtered and purified by chromatography. The eluate fractions are lyophilized to obtain the amine as an acetic acid, trifluoroacetic acid or hydrochloric acid addition salt.

The N-alkylated or benzylated compounds may be prepared using any suitable known procedure for preparing secondary or tertiary amines. The N-benzyl compound is best prepared by first preparing a Schiff base with benzaldehyde and thereafter reducing with conventional reducing agents such as those previously noted in connection with the reduction of the nitrile although milder reducing agents may be employed.

When the desired alkyl group on the nitrogen is methyl, the carbon may be introduced by formylating, followed by reduction of the hydroxymethyl group with sodium cyanoborohydride or other reducing agent. When the desired alkyl group on the nitrogen is a higher alkyl, a preferred procedure is a reductive alkylation of an N-benzyl derivative with an aldehyde and a reducing agent such as sodium cyanoborohydride, and purifying the product with reverse phase chromatography to obtain a benzyl and a higher alkyl substituted tertiary amine. The benzyl group may be removed by hydrogenation using palladium on carbon or other suitable catalyst.

When the alkyl groups are the same, the same general procedure is preferably employed. Although alkyl halide or sulfate may be employed, these are best for quaternary salts.

When all substituents on the nitrogen are the same, the starting amine may be the primary amine. For mixed amines, it is preferable to enter the specific groups first since alkylation using an alkylating agent is more difficult to control.

To prepare the aminoalkyl ethers or ammoniumalkyl ethers, camphorsulfonic acid is added to the solution containing cyclohexapeptidyl propanolamine compound (Compound G), the appropriate ammonium- or amninoalkanol or ammonium- or amino-alkylthiol hydrochloride salt or N-carbobenzyloxy (CBZ) protected aminoalkanol or aminoalkylthiol and camphorsulfonic acid or hydrogen chloride are mixed together and the mixture allowed to stir at room temperature for one to seven days. The progress of the reaction is conveniently monitored by HPLC using acetonitrile/water as the eluting agent. After the reaction is substantially complete, the reaction mixture is diluted with water and the resulting solution applied to a reverse phase flash silica gel column and eluted with an appropriate mixture of acetonitrile and water to obtain the desired amine compound, or the CBZ protected amine compound. In the case of the latter, the protective CBZ group is removed by hydrogenolysis.

A large excess of the ammonium- or amino-alkanol or ammonium or amino-alkylthiol is employed, preferably of the order of one-hundred molar equivalents. The amount of camphorsulfonic acid or hydrogen chloride is about two moles for every mole of the cyclohexapeptidyl propanolamine. The reaction medium is a suitable aprotic solvent such as dimethylsulfoxide (DMSO) or dimethylformamide (DMF) or dioxane, or combinations thereof.

For monitoring the progress of the reaction, an analytical "ZORBAX" (DuPont) column with 10 to 50 percent aqueous acetonitrile containing 0.1 percent trifluoroacetic acid (TFA) or acetic acid is suitable. For preparative purification, a reverse phase column such as "LICHROPREP" C18 of particle size 40–63 microns with 5–15 percent aqueous acetonitrile to remove solvent and 10 to 50 percent acetonitrile (containing 0.1% TFA or acetic acid) to elute the product is useful.

The compounds of the present invention are active against many fungi and particularly against Candida, Aspergillus and Cryptococcus species. The antifungal properties may be illustrated with the minimum fungicidal concentration (MFC) determination against certain Candida and Cryptococcus organisms in a microbroth dilution assay carried out in a Yeast Nitrogen Base (Difco) medium with 1 percent dextrose (YNBD).

In a representative assay, Compound Xa is solubilized in 100 percent dimethyl sulfoxide (DMSO) at an initial concentration of 5 mg/L. Once dissolved, the drug stock is brought to a concentration of 512 mg/L by dilution in water such that the final DMSO concentration is about 10 percent. The solution is then dispensed via a multichannel pipetter into the first column of a 96-well plate (each well containing 0.075 ml of YNBD), resulting in a drug concentration of 256 mg/L. Compounds in the first column are diluted 2-fold across the rows yielding final drug concentrations ranging from 256 mg/L to 0.12 mg/L.

Four-hour broth cultures of organisms to be tested are adjusted using a spectrophotometer at 600 nm to equal a 0.5 McFarland Standard. This suspension is diluted 1:100 in YNBD to yield a cell concentration of $1-5 \times 10^4$ colony forming units (CFU)/ml. Aliquots of the suspension (0.075 ml) are inoculated into each well of the microtiter plate resulting in a final cell inoculum of $5-25 \times 10^3$ CFU/ml and final drug concentrations ranging from 128 mg/L to 0.06 mg/L. Each assay includes one row for drug-free control wells and one row for cell-free control wells.

After 24 hours of incubation, the microtiter plates are shaken gently on a shaker to resuspend the cells. The MIC-2000 inoculator is used to transfer a 1.5 microliter sample from each well of the 96-well microtiter plate to a single reservoir inoculum plate containing Sabouraud dextrose agar (SDA). The inoculated SDA plates are incubated for 24 hours at 35° C.

The in vivo effectiveness of the compounds against fungi may be demonstrated with Compound X-a.

Growth from an overnight SDA culture of *Candida albicans* MY 1055 is suspended in sterile saline and the cell concentration determined by hemacytometer count and the cell suspension adjusted to $3.75 \times 10^5$ cells/ml. Then 0.2 milliliter of this suspension is administered I.V. in the tail vein of mice so that the final inoculum was $7.5 \times 10^4$ cells/mouse.

The assay then is carried out by administering aqueous solutions of Compound X-a at various concentrations intraperitoneally (I.P.), twice daily (b.i.d.) for four consecutive days to 18 to 20 gram female DBA/2 mice, which previously has been infected with *Candida albicans* in the manner described above. Distilled water is administered I.P. to *C. albicans* challenged mice as controls. After seven days, the mice are sacrificed by carbon dioxide gas, paired kidneys are removed aseptically and placed in sterile polyethylene bags containing 5 milliliters of sterile saline. The kidneys are homogenized in the bags, serially diluted in sterile saline and aliquots spread on the surface of SDA plates. The plates are incubated at 35° C. for 48 hours and yeast colonies are enumerated for determination of colony forming units (CFU) per gram of kidneys.

The compounds of the present invention may also be useful for inhibiting or alleviating *Pneumocystis carinii* infections in immune compromised patients. The efficacy of the compounds of the present invention for therapeutic or anti-infective purposes may be demonstrated in studies on immunosuppressed rats.

In a representative study, the effectiveness of Compound X-a is determined. Sprague-Dawley rats (weighing approximately 250 grams) are immunosuppressed with dexamethasone in the drinking water (2.0 mg/L) and maintained on a low protein diet for seven seeks to induce the development of Pneumocystis pneumonia from a latent infection. Before drug treatment, two rats are sacrificed to confirm the presence of *Pneumocystis carinii* pneumonia (PCP). Five rats (weighing approximately 150 grams) are injected twice daily for four days subcutaneously (sc) with Compound X-a in 0.25 ml of vehicle (distilled water). A vehicle control is also carried out. All animals continue to receive dexamethasone in the drinking water and low protein diet during the treatment period. At the completion of the treatment, all animals are sacrificed, the lungs are removed and processed, and the extent of disease determined by microscopic analysis of stained slides.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1 percent by weight of Compound X or one of the components. Concentrate compositions suitable for dilutions prior to use may contain 90 percent or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound X with the components suitable for the medium desired.

Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with a lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and for injecton take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is for antifungal use any method of administration may be employed.

When the compound is to be employed for control of pneumocystis infections any method may be employed although it may be desirable to directly treat lung and bronchi. In such administration inhalation methods are employed. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of Compound X in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE I

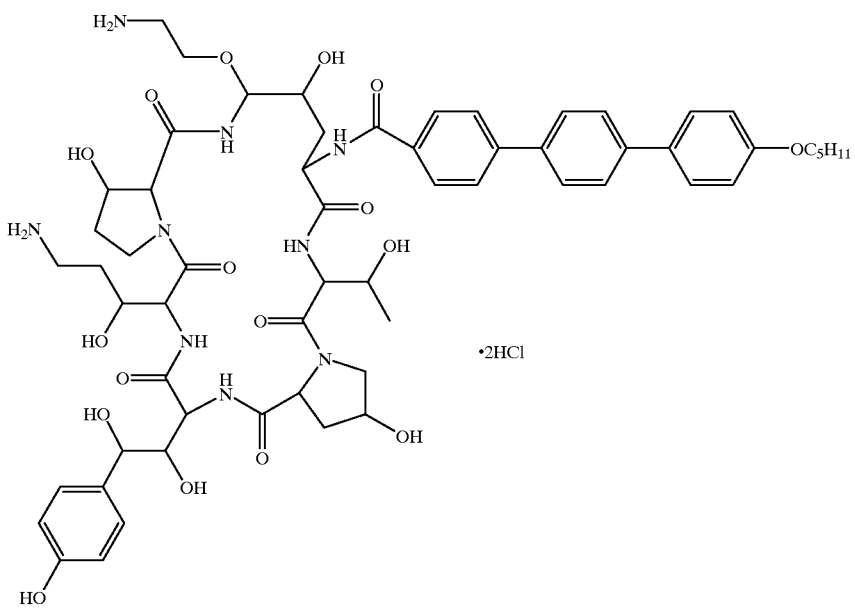

Seq. ID No.1

A. Preparation of Intermediate Nitrile Compound

A solution of the lipopeptide (where $R_1$, $R_2$, $R_3$, $R_4$=OH, $R_5$=H, $R_6$=$CH_3$, $R^I$=4" (n-pentyloxy-[1,1':4',4"-terphenyl]-4-yl) (1.0 eq) is prepared in sieve-dried DMF and approximately 3 molar equivalents of cyanuric chloride is added in one portion. After 5–6 minutes, the reaction is quenched with 10 molar equivalents of aqueous sodium acetate. The reaction mixture is diluted with 50% aqueous acetonitrile and purified by preparative HPLC (C18 "ZORBAX" DuPont, step gradient starting at 70/30:$H_2O$/$CH_3CN$/0.1% TFA) and the appropriate fractions are lyophilized to give the desired product as a solid (MW=1151.25).

B. Preparation of the Amine Compound

To a solution of the above nitrile compound (1.0 eq) in methanol is added cobalt (II) chloride (4.0 eq). Next, $NaBH_4$ (20 eq) is added cautiously and in several portions. The black reaction is stirred for several hours at which time sufficient 2N hydrochloric acid is added to effect dissolution of the precipitate. The resultant solution is diluted with water and purified by preparative HPLC (C18 "ZORBAX", step gradient starting at 70/30:$H_2O$/$CH_3CN$/0.1% TFA). The appropriate fractions are combined and lyophilized to obtain the desired water soluble product (MW=1269.32).

C. Preparation of Aminoethyl Ether

The propanolamine compound prepared above (1.0 eq), ethanolamine hydrochloride (200 eq) and camphorsulfonic acid (1.0 eq) are dissolved in a small amount of DMF and stirred at room. temperature for 1 to 4 days until the starting propanolamine is consumed. The mixture is diluted with water and purified by preparative HPLC (C18 "ZORBAX", step gradient starting at 70/30:$H_2O$/$CH_3CN$/0.1% TFA) and the appropriate fractions are combined, frozen and lyophilized to give a solid. The material is dissolved in water and passed down an anion exchange column (Cl-form) and the eluate lyophilized to obtain the desired product as a hydrochloride salt (MW=1271.27).

EXAMPLE II

Seq. ID No.1

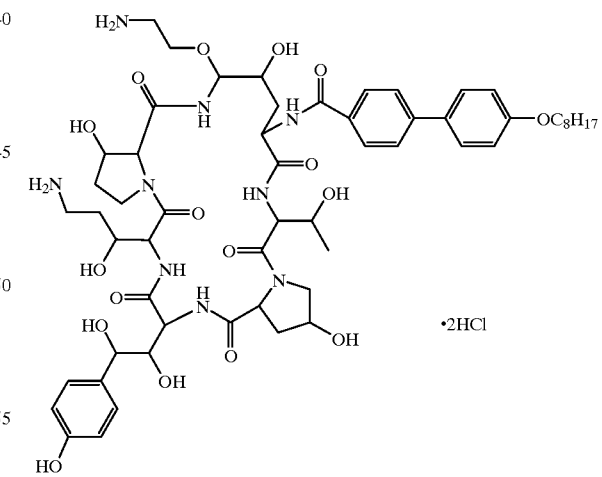

In a manner similar to steps A, B and C above in example I but starting with the lipopeptide (where $R_1$, $R_2$, $R_3$, $R_4$=OH, $R_5$=H, $R_6$=$CH_3$, $R^I$=4'-n-octyloxy[1,1'-biphenyl]4-yl), the corresponding bisamine compound may be prepared (MW=1237.25).

EXAMPLE III

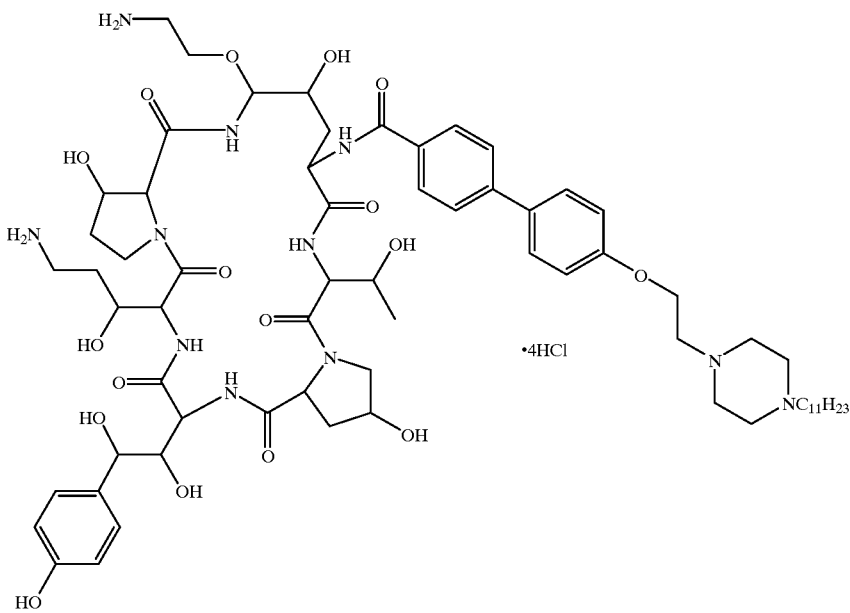

Seq. ID No.1

In a manner similar to steps A, B and C above in Example I but starting with the lipopeptide ($R_1$, $R_2$, $R_3$, $R_4$=OH, $R_5$=H, $R_6$=$CH_3$, $R^I$=4'-(2-[4-undecylpiperazin-1-yl])ethoxy)[1,1'-biphenyl]-4-yl, the corresponding tetraamine compound may be prepared (MW=1464.5).

EXAMPLE IV

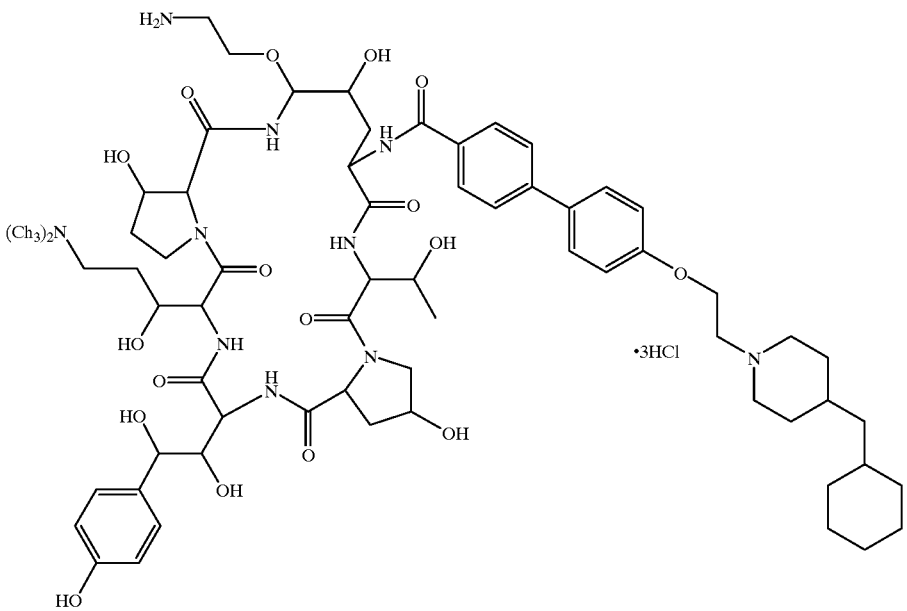

A. Preparation of Intermediate Nitrile Compound

A solution of the lipopeptide (where $R_1$, $R_2$, $R_3$, $R_4$=OH, $R_5$=H, $R_6$=$CH_3$, $R^I$=4'-(2-[4-cyclohexylmethylpiperidin-1-yl]ethoxy)[1,1'biphenyl]4-yl), (1.0 eq) is prepared in sieve-dried DMF and approximately 3 molar equivalents of cyanuric chloride is added in one portion. After 5–6 minutes, the reaction is quenched with 10 molar equivalents of aqueous sodium acetate. The reaction mixture is diluted with 50% aqueous acetonitrile and purified by preparative HPLC (C18 "ZORBAX", step gradient starting at 70/30:$H_2O$/$CH_3CN$/ 0.1% TFA) and the appropriate fractions are lyophilized to give the desired product as a solid (MW=1326.40).

B. Preparation of the Amine Compound

To a solution of the above nitrile compound (1.0 eq) in methanol is added cobalt (II) chloride (4.0 eq). Next, $NaBH_4$ (20 eq) is added cautiously and in several portions. The black reaction is stirred for several hours at which time sufficient 2N hydrochloric acid is added to effect dissolution of the precipitate. The resultant solution is diluted with water and purified by preparative HPLC (C18 "ZORBAX", step gradient starting at 70/30:$H_2O$/$CH_3CN$/0.1% TFA). The appropriate fractions are combined and lyophilized to obtain the desired product (MW=1444.46).

C. Preparation of the N-Benzyloxycarbonylaminoethyl Ether

The propanolamine compound prepared above (1.0 eq), N-(benzyloxycarbonyl)ethanolamine (25 eq) and camphorsulfonic acid (1.0 eq) are dissolved in a small amount of dioxane-DMF-DMSO (10:2:1) and stirred at room temperature for about 24 hours. The mixture is neutralized by the addition of aqueous sodium bicarbonate and purified by preparative HPLC (C18 "ZORBAX", step gradient starting at 70/30:$H_2O$/$CH_3CN$/0.1% TFA). The appropriate fractions are combined, frozen and lyophilized to give solid (MW=1621.66).

D. Dimethylation of Reduced Glutamine

To a solution of the diamine compound (1 eq) in acetonitrile prepared above, is added 50 eq of 37% aqueous formaldehyde. Next, sodium cyanoborohydride (8 eq) is added and the mixture stirred at room temperature for 10 minutes. The reaction is neutralized with acetic acid and purified by preparative HPLC (C18 "ZORBAX", step gradient starting at 70/30:$H_2O$/$CH_3CN$/0.1% TFA). The appropriate fractions are combined and lyophilized to obtain the desired product (MW=1649.72).

E. Hydrogenolysis of Carbobenzyloxy Group

The compound prepared in step D is dissolved in glacial acetic acid and hydrogenated at one atmosphere using 10% Pd-C as catalyst (25 weight percent) for several hours. The reaction mixture is filtered to remove the catalyst and concentrated in vacuo. Purification by preparative HPLC (C18 "ZORBAX", step gradient starting at 70/30:$H_2O$/$CH_3CN$/0.1% TFA)) followed by lyophilization of the desired fractions gives a solid. This material is dissolved in water and passed down an anion exchange column (Cl-form) and the eluate lyophilized to obtain the desired product as a hydrochloride salt (MW=1396.91)

EXAMPLE V

In operations carried out as described in Examples I–II, the following compound in which $R_1$, $R_2$ and $R_4$ are OH, $R_6$ is $CH_3$ and the other substituents are as set forth below are prepared:

| Compound | $R_3$ | $R_5$ | $R^{I*}$ | $R^{II}$ | $R^{III}$ | SEQ ID NO |
|---|---|---|---|---|---|---|
| V-A | $H_2NCH_2CH_2O$— | H | p,p'-φ-φ-O—$(CH_2)_2$—N⟨ ⟩N—$C_{11}H_{23}$ | H | H | 1 |
| V-B | $H_2NCH_2CHCH_2O$— (with $NH_2$) | H | p,p'-φ-φ-O—$(CH_2)_2$—N⟨ ⟩N—$C_{11}H_{23}$ | H | H | 1 |
| V-C | $H_2NCH_2CHCH_2O$— (with $NH_2$) | H | p,p'-φ-φ-O—$C_8H_{17}$ | $CH_3$ | $CH_3$ | 1 |
| V-D | $(CH_3)_3\overset{\oplus}{N}CH_2CH_2O$— $Cl^{\ominus}$ | H | p,p'-φ-φ-O—$C_8H_{17}$ | $CH_3$ | H | 1 |
| V-E | $H_2NCH_2CH_2S$— | H | p,p'-φ-φ-O—$C_8H_{17}$ | $CH_3$ | H | 1 |
| V-F | $H_2N-\overset{NH}{\overset{\|}{C}}-NH-(CH_2)_2-O-$ | $CH_3$ | p,p'-φ-φ-φ-O—$C_5H_{11}$ | H | H | 2 |

*p,p'-φ-φ is 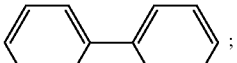 ;

*p,p'-φ-φ-φ is 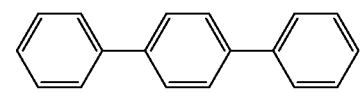

EXAMPLE VI

In operations carried out as described in ffie preceding examples, the following compounds may be prepared in which $R^I$ is p,p'-φ-φ-$OC_5$-$H_{11}$, $R^{II}$ and $R^{III}$ are H:

| Compound | R1 | R2 | R3 | R4 | R5 | R6 | SEQ ID |
|---|---|---|---|---|---|---|---|
| VI-A | OH | OH | $H_2N(CH_2)_2S-$ | OH | H | $CH_3$ | 1 |
| VI-B | H | H | $(CH_2)_5N(CH_2)_2O-$ | H | $CH_3$ | $CH_3$ | 5 |
| VI-C | OH | OH | $C_6H_5CH_2NH(CH_2)_2O-$ | OH | OH | $CH_3$ | 6 |
| VI-D | H | OH | $H_2NCH_2CH_2O-$ | OH | H | H | 7 |
| VI-E | H | OH | $(CH_3)_2NCH_2CH_2O-$ | OH | H | $CH_3$ | 29 |
| VI-F | H | OH | $H_2N(CH_2)_3S-$ | OH | $CH_3$ | H | 3 |
| VI-G | OH | OH | $H_2N-C(=NH)-NH-CH_2CH_2O-$ | OH | H | $CH_3$ | 1 |
| VI-H | OH | OH | $H_2NCCH(ONH_2)-CH_2O-$ | OH | $CH_3$ | $CH_3$ | 2 |

EXAMPLE VII 1000 hard gelatin capsules each containing 500 mg of Compound X are prepared from the following formulation:

| Compound | Grams |
|---|---|
| Compound X (of Example I) | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE VIII

An aerosol composition may be prepared having the following formulation:

| | Per Canister |
|---|---|
| Compound X (of Example II) | 24 mg |
| Lecithin NF Liquid Concentrated | 1.2 mg |
| Trichlorofluoromethane, NF | 4.026 g |
| Dichlorodifluoromethane, NF | 2.15 g |

EXAMPLE VIII 250 milliliters of an injectible solution may be prepared by conventional procedures having the following formulation:

| | |
|---|---|
| Dextrose | 12.5 g |
| Water | 250 ml |
| Compound X | 400 mg |

The ingredients are blended and thereafter sterilized for use.

Preparation of Starting Materials:

The starting materials for the compounds are derivatives of natural products. The various nuclei are obtainable by cultivation of the appropriate organism, isolating the natural product which will have the appropriate nucleus with a different side chain, then deacylating the lipophilic group, recovering the deacylated cyclopeptide and acylating said cyclopeptide with the appropriate active ester $R^ICOX$ to obtain compound E as hereinafter detailed.

The natural product which differs in the side chain from the starting material are hereafter identified with a prime after the E identification. Thus, the natural product corresponding to starting material "E-1" is identified below as "E'-1"

E'-1 may be produced by cultivating Zalerion arboricola ATCC 20868 in a nutrient medium enriched in mannitol as the primary source of carbon as described in U.S. Pat. No. 5,021,341, Jun. 4, 1991.

E'-2 may be produced by cultivating Zalerion arboricola ATCC 20868 in nutrient medium as described in U.S. Pat. No. 4,931,352, Jun. 5, 1990 or in nutrient medium enriched in glycerol as described in U.S. Pat. No. 4,968,608, Nov. 6, 1990.

E'-2 nucleus with a different R may be produced by cultivating Acrophialophora limonispora in nutrent medium as described in U.S. Pat. No. 4,173,629.

E'-3 and E'-7 may be produced by cultivating Cryptosporiopsis ATCC 20594 in nutrient medium as described by Pache et al in 13th ICC (1983), PS 4.8/3, Part 115, Abstract No. 10 and PCT WO 82/00587.

E'-4, E'-5 and E'-6 may be produced by cultivating Zalerion arboricola ATCC 20868 in nutrient medium.

When $R_1$ is H, $R_2$, $R_3$ and $R_4$ are OH, $R_5$ is H or $CH_3$ and $R_6$ is $CH_3$, the starting material may be made using another starting material, in which $R_1$, $R_2$, $R_3$ and $R_4$ are OH, $R_5$ is H and $R_6$ is $CH_3$ (i.e., E'-') and reducing R1 by methods known to the skilled in the art. Conveniently this may be carried out by adding trifluoroacetic acid to the material and triacetoxyborohydride and mixing together to obtain a product and thereafter purifying the product by conventional methods such as by HPLC.

Starting materials in which $R^I$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as also described in Experentia 34, 1670 (1978) or U.S. Pat. No. 4,293,482, and recovering the deacylated cyclopeptide and thereafter acylating the deacylated cyclopeptide by mixing together with an appropriate active ester $R^ICOX$ to obtain Compound E with tile desired acyl group using conventional procedures. Methods are also described in U.S. Pat. Nos. 4,287,120 and 4,293,489.

The active ester R'COX for the side chain R' may be prepared by methods known to the skilled chemist as illustrated in the following examples. Although any active ester is appropriate, the compounds are illustrated with pentafluorophenyl esters.

Preparation of Alkoxyterphenyl Side Chains

The terphenylcarboxylic acid esters may be prepared through the following sequence of reactions, illustrated with a specific example as follows:

A. Preparation of pentyloxyphenyl—substituted—terphenylcarboxylic acid:

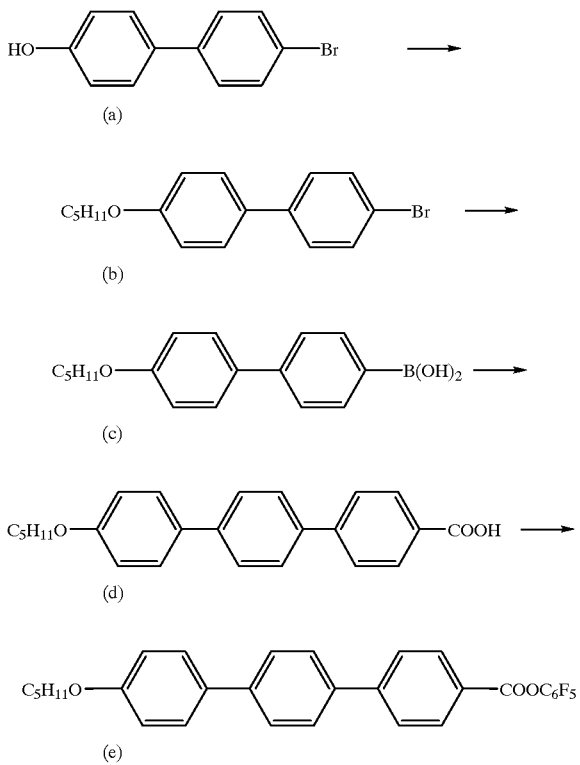

Part A: 4-(4-n-Pentyloxyphenyl)bromobenzene.

To a stirred solution of 25.5 g of 4-(4-bromophenyl) phenol. (Compound (a)) in 400 mL of dimethylsulfoxide was added 40.9 mL of 2.5 N NaOH, followed by 12.7 mL of n-pentyl bromide, and the resulting mixture heated at 70° C. for 18 hours to obtain in the mixture, compound (b). The mixture was partitioned between 1000 mL of ethyl acetate and 500 mL water and from the organic phase after washing with water and brine, and drying was obtained 30.9 grams of Compound (b) as a white solid.

'H NMR (400 MHz, DMSO-d6) δ 0.93 (t, J=7.2 Hz, 3H), 1.41 (m, 4H), 1.79 (m, 2H), 3.97 (t, J=6.6 Hz, 2H) 6.94 (d, J=8.8 Hz, 2H), 7.39 (d, J=8.6 Hz, 2H), 7.45 (d, J=8.8 Hz, 2H), 7.51 (d, J=8.6 Hz, 2H).

Part B: 4-(4-n-Pentyloxyphenyl)phenylboronic acid.

To a stirred suspension of 1.0 grams of Compound (b) in 20mL anhydrous tetrahydrofuran at −78° C. under a nitrogen atmosphere was added 1.32 mL of n-butyl lithium 2.5M in hexanes. After 15 minutes 0.760 mL of tri-isopropyl borate was added and the stirring continued at −78° C. for 15 minutes and then at 25° C. for 40 minutes. The mixture is acidified and partitioned between ether and water to obtain the boronic acid compound (c) in the reaction mixture. The compound was recovered by washing with water and brine and drying to obtain 750 mg of 4-(4-n-pentyloxyphenyl) phenylboronic acid as white solid with following $^1$H NMR.

$^1$H NMR (400 MHz, DMSO-d6) δ 0.89 (t, J=7.2 Hz, 3H), 1.38 (m, 4H), 1.72 (m, 2H), 3.99 (t, J=6.5 Hz, 2H) 6.99 (d, J=8.8 Hz, 2H), 7.57 (d, J=8.2 Hz, 2H), 7.60 (d, J=8.8 Hz, 2H), 7.83 (d, J=8.2 Hz, 2H)

Part C: Pentafluorophenyl 4"-(n-pentyloxy)-[1,1':4',4"-terphenyl]-4-carboxylate

To a stirred mixture of 1.0 g of the boronic acid and 0.0874 mL of 4-iodobenzoic acid in 11 mL ethanol and 30 mL toluene was added 5.3 mL of a 2M aqueous solution of sodium carbonate followed by 204 mg tetrakis (triphenylphosphine)palladium and the reaction mixture heated under reflux (100° C.) for 18 hours. Thereafter, the mixture was cooled, acidified and partitioned between ethyl acetate and water. The organic phase. was washed with water and brine and dried, then filtered through a bed of celite to obtain after removal of solvent and purification with flash silica gel chromatography to obtain 4'-(n-pentyloxy)-[1,1':4',4"-tephenyl-4-carboxylic acid.

$^1$H NMR (400 MHz, DMSO-d$_6$) δ 0.89 (t, 3H), 1.37 (m, 4H), 1.72 (m, 2H), 3.98 (t, 2H) 7.01 (d, 2H).

To a mixture of 4'-(n-pentyloxy)-[1,1':4',4"-terphenyl]-4-carboxylic acid (10.5 mmol) and dicyclohexylcarbodiimide (10.5 mmol) in ethyl acetate at 0° C. is added pentafluorophenol (11.5 mmol). The mixture is stirred at 25° C. for a period of 18 h, producing a precipitate. The mixture is filtered. The filtrate is washed with water and brine and dried with magnesium sulfate. The solvent is removed in vacuo to obtain pentafluorophenyl 4"-(n-pentyloxy)-[1,1':4',4"-terphenyl]4-carboxylate, $C_{30}$-$H_{23}F_5O_3$, M.W.=526.5.

Preparation of Alkoxy Biphenyl Side Chains

The biphenylcarboxylic acid esters may be obtained through the following sequence of reactions illustrated as follows:

A. Preparation of Octyloxybiphenylcarboxylic Acid

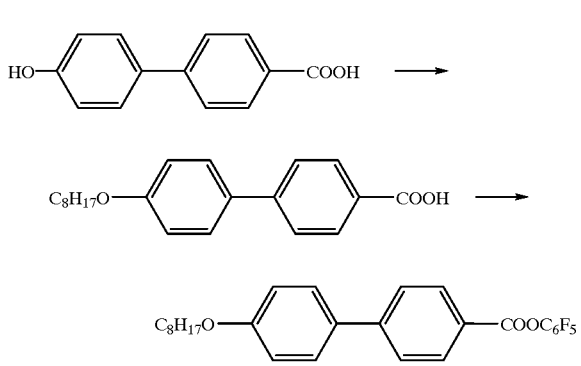

n-Octyl bromide (0.102 mol) is added to a solution of 4-(4-hydroxyphenyl)benzoic acid (0.102 mol) and 2.5N sodium hydroxide (0.102 mol) and the mixture stirred at 70° C. for a period of 18 hours. The reaction mixture is allowed to cool and then acidified to pH 3 and partitioned between ethyl acetate and water. The organic phase is washed with water and brine and the solvent then removed to obtain the 4'-n-octyloxy[1,1'-biphenyl]-4-ylcarboxylic acid, $C_{21}H_{23}O_3$, M.W. 326.4.

B. Preparation of Pentafluorophenyl Ester

Pentafluorophenol (11.5 mmol) is added at 0° to a mixture of 10.5 mmol 4'-n-octyloxy[1,1'-biphenyl]-4-ylcarboxylic acid and 10.5 mmol of dicyclohexylcarbodiimide in ethyl acetate. The mixture is stirred at 25° C. for a period of 18 hours whereupon a precipitate is formed. The reaction mixture is filtered, the filtrate washed with water and brine and dried, the solvent removed in vacuo to obtain pentafluorophenyl 4'-n-octyloxy[1,1'-biphenyl]-4-ylcarboxylate, $C_{27}H_{25}F_5O_3$, M.W. 492.5.

Preparation of Aminoethyloxybiphenyl Side Chains

Preparation of 4'-(2-[4-Cyclohexylmethylpiperidin-1-yl]ethoxy)-[1,1'-biphenyl]-4-ylcarboxylic acid, Pentafluorophenyl Ester

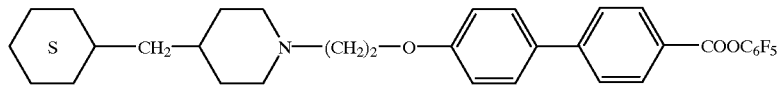

Part A: Preparation of 4-Cyclohexylmethylpiperidine

4-Benzylpiperidine is dissolved in glacial acetic acid containing $PtO_2$ (approximately 50 wt percent). A Paar hydrogenator is used and the reaction vessel is flushed with $H_2$ and pressurized to 3 atm. The mixture is shaken for sufficient time to give reduction of the aromatic ring to the fully saturated product which is determined by the uptake of 3 molar equivalents of $H_2$. The black solid is filtered and the acetic acid removed by evaporation under reduced pressure to obtain the product as an acetate salt.

Part B: Preparation of 1-(2-Hydroxyethyl)-4-cyclohexylmethylpiperidine

The product from Part A (1.0 eq) is dissolved in dichloromethane containing an equimolar amount of diisopropylethyl amine. Ethylene oxide (10 eq) is added and the mixture is stirred until starting material is consumed. The desired product is obtained by removal of the solvent in vacuo followed by purification by column chromatography.

Part C: Preparation of 4'-(2-[4-cyclohexylmethylpiperidine-1-yl]ethoxy)-[1,1'-biphenyl]-4-ylcarboxylic Acid 4'-Hydroxy-[1,1-biphenyl-4-ylcarbonylic acid methyl ester (1.0 eq) is dissolved in dichloromethane and triphenylphosphine (1.3 eq) and the hydroxyethyl compound (1.0 eq) from Part B is added. Next, diethyl azodicarboxylate (1.3 eq) is added and the mixture is stirred until starting material is consumed. The mixture is diluted with dichloromethane and washed with water. The organic layer is dried with $MgSO_4$ and filtered. The solvent is removed in vacuo and the residue is dissolved in ethanol. An excess of 3N sodium hydroxide is added and the mixture stirred for several hours. The reaction is neutralized with 2N HCl and is extracted with ethyl acetate. The ethyl acetate layer is dried with $MgSO_4$, filtered and the solvent vaporized under reduced pressure. The desired product is obtained in substantially pure form by column chromatography.

Part D: Preparation of the Pentafluorophenyl Ester

The carboxylic acid (1.0 eq) and dicyclohexylcarbodiimide (1.0 eq) are dissolved in ethyl acetate and the solution is cooled to 0° C. Pentafluorophenol (1.05 eq) is added, the ice bath then is removed and the reaction stirred at ambient temperature for 18–24 h. An equal volume of ether is added, the mixture is filtered and the solvent removed in vacuo. The product (MW=587.64) is sufficiently pure to be utilized "as is" for nucleus acylation.

Preparation of 4'-(2-[4-Undecylpiperizin-1-yl]-ethoxy)[1,1-biphenyl]-4-ylcarboxylic acid, Pentafluorophenyl Ester

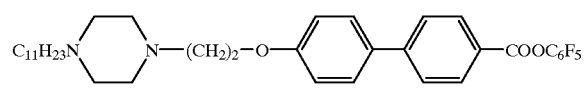

Part A: Preparation of 4-Undecylpiperazine

Excess piperazine (5 eq) and 1-bromoundecane (1.0 eq) are dissolved in dichloromethane and allowed to react overnight. The mixture is extracted with aqueous sodium bicarbonate and the organic layer dried with sodium sulfate. The mixture is filtered, the solvent removed in vacuo and the residue purified by column chromatography.

Part B: Preparation of 1-(2-Hydroxvethyl)4-undecylpiperazine

The substituted piperazine above (1.0 eq) is dissolved in n-propanol and bromoethanol (1.0 eq) is added along with diisopropylethyl amine (1.1 eq). After several hours, the solvent is removed in vacuo and the residue dissolved in dichloromethane. The organic layer is washed with water and then aqueous sodium bicarbonate. The organic layer is dried with $MgSO_4$ and filtered. Removal of the solvent in vacuo is followed by purification by column chromatography.

Part C: Preparation of the Carboxylic Acid

The procedure is essentially the same as describe in Part C above except that the hydroxyethyl piperazine from above is substituted for the hydroxyethyl piperidine.

Part D: Preparation of the Pentafluorophenyl Ester

The procedure is identical to Part D from above except that the piperazine acid yl ethoxy substituted biphenylyl is used. The product (MW=646.75) is sufficiently pure to be utilized "as is" in nucleus acylation.

What is claimed is:

1. A compound represented by the formula (Seq. ID No. 1–7, 29);

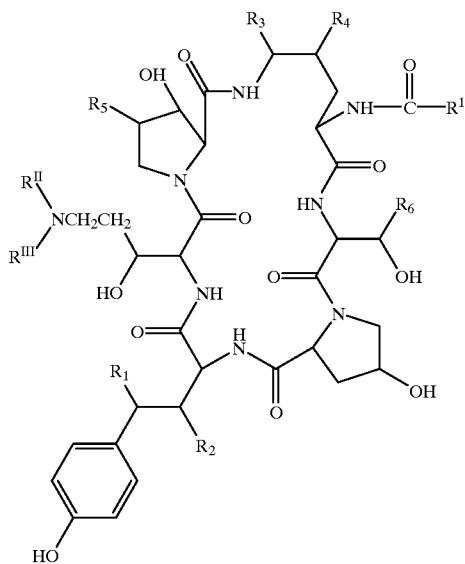

or its acid addition salt wherein;
$R_1$ is H or OH;
$R_2$ is H or OH;
$R_3$ is $QC_nH_{2n}NR^VR^{VI}$, $QC_nH_{2n}NR^VR^{VI}R^{VII+}Y^-$, or $Q(CH_2)_{1-3}CR^{VIII}R^{IX}NHR^X$;
$R_4$ is H or OH;
$R_5$ is H;
$R_6$ is H or $CH_3$;

$R^I$ is

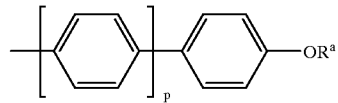

wherein
$R^a$ is $C_1$–$C_{10}$ alkyl; or
$(CH_2)_qNR^bR^c$ wherein $R^b$ and $R^c$ are independently H, $C_1$–$C_{10}$ alkyl or $R^b$ and $R^c$ taken together are

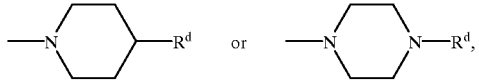

wherein
$R^d$ is $C_1$–$C_{16}$ alkyl, phenyl or benzyl;
$R^{II}$ is H, $C_1$–$C_4$ alkyl or benzyl;
$R^{III}$ is H, $C_1$–$C_4$ alkyl or benzyl;
$R^{IV}$ is $R^{II}$ and $R^{III}$ taken together as —$(CH_2)_4$— or —$(CH_2)_5$—;
$R^V$ is H, $C_1$–$C_4$ alkyl or benzyl;
$R^{VI}$ is H, $C_1$–$C_4$ alkyl or benzyl, or $R^V$ and $R^{VI}$ together are —$(CH_2)_4$— or —$(CH_2)_5$—;
$R^{VII}$ is H or $C_1$–$C_4$ alkyl;
$R^{VIII}$ is H, $(CH_2)_mH$, $(CH_2)_mOH$, $(CH_2)_mNH_2$ or COX wherein X is $NH_2$, OH or $O(CH_2)_mH$;
$R^{IX}$ is H, $(CH_2)_mH$, or together with $R^{VIII}$ is =O (carbonyl);
$R^X$ is H (except when $R^{VIII}$ and $R^{IX}$ are H), C(=NH)$NH_2$, C(=NH)$CH_2)_{0-3}$H, $CO(CH_2)_{0-3}$H, $CO(CH_2)_m$$NH_2$, $(CH_2)_{2-4}$OH or $(CH_2)_{2-4}NH_2$;
Q is O or S;
Y is an anion of a pharmaceutically acceptable salt, and each m is independently an integer from 1 to 3, inclusive;
n is an integer from 2 to 4, inclusive;
p is 1 or 2, and
q is an integer from 2 to 4, inclusive.

2. A compound according to claim 1 having the formula
(Seq ID No. 1)
Seq ID No 1
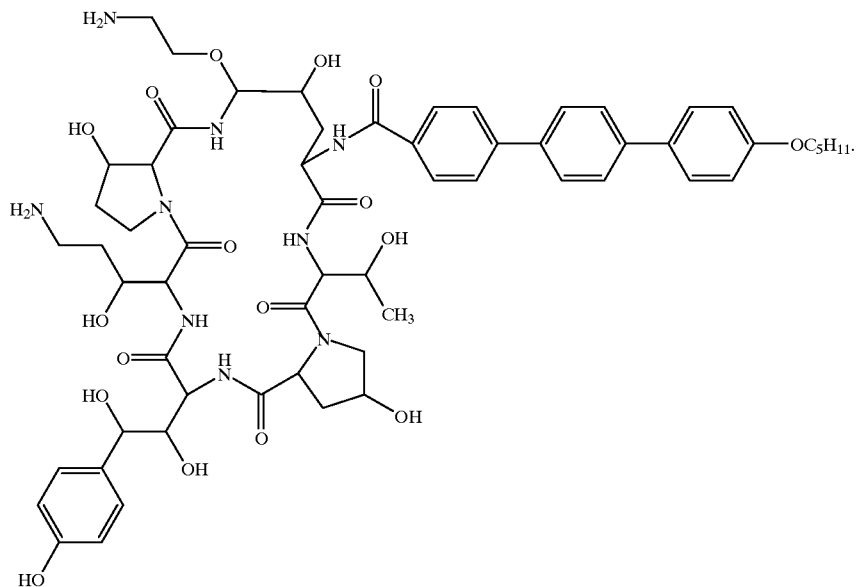
3. A compound according to claim 1 having the formula 30
(Seq. ID No. 1)
Seq ID No 1
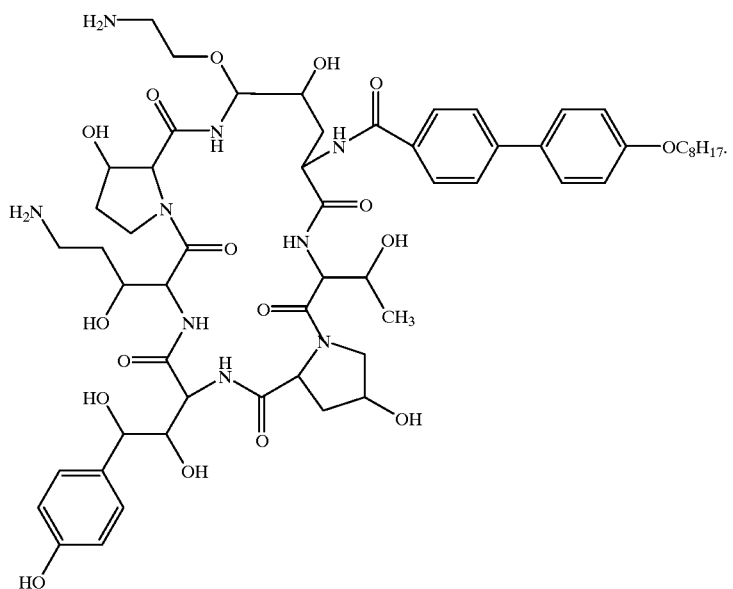

4. A compound according to claim 1 having the formula (Seq ID No. 1)
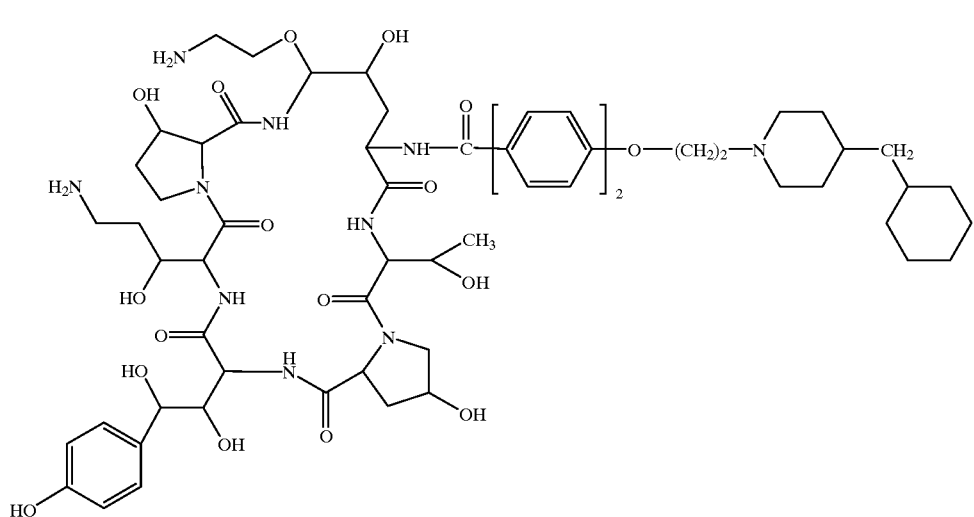
or its acid addition salts.
5. A compound according to claim 1 having the formula
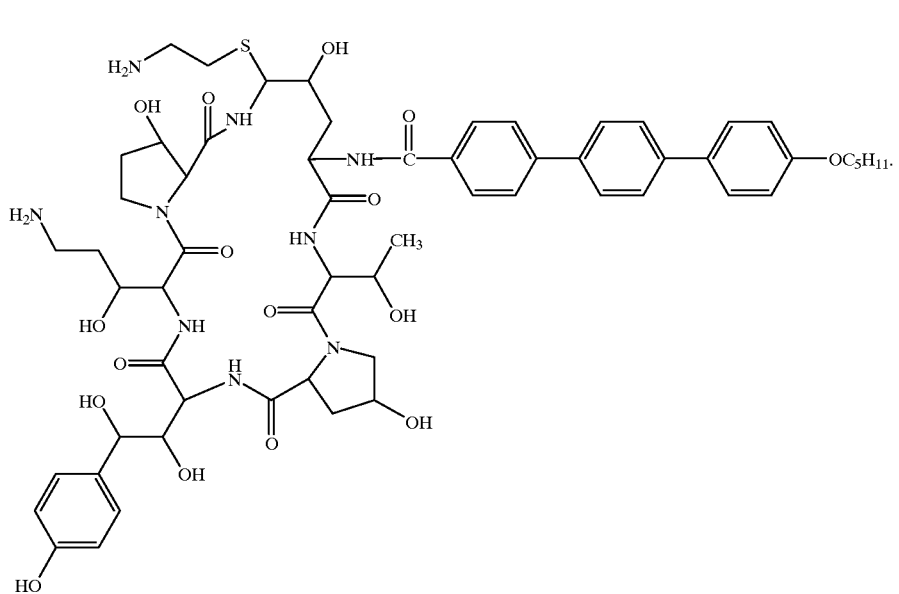

6. A compound according to claim 1 having the formula

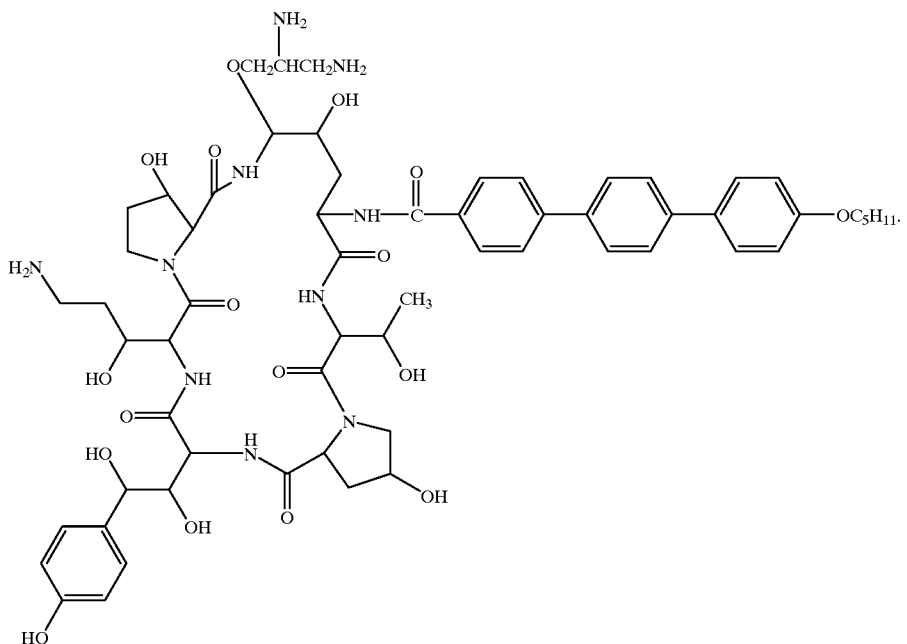

Seq ID No 1

7. A compound according to claim 1 having the formula
(Seq ID No. 1)

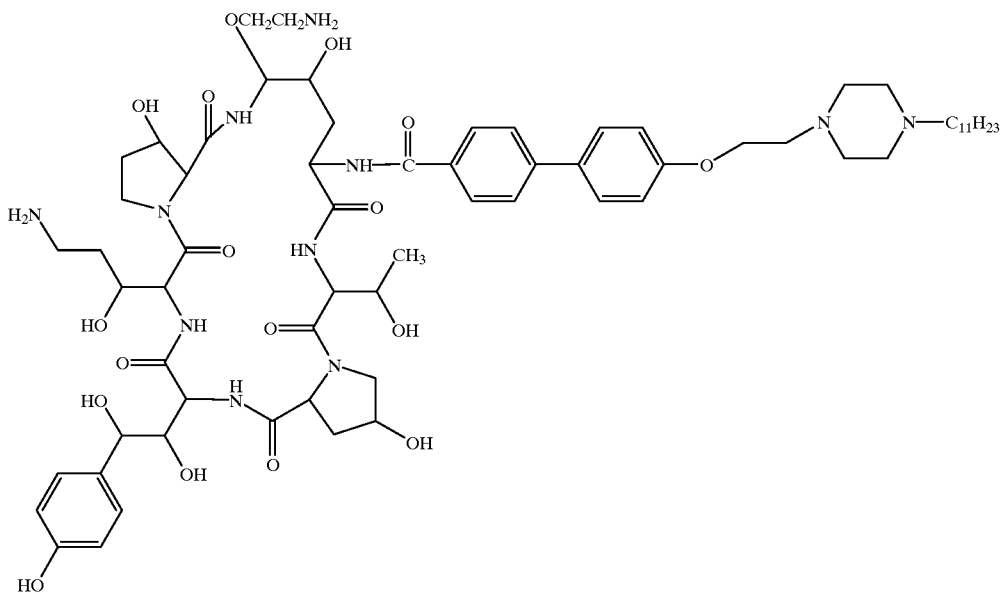

Seq ID No1

8. An antibiotic composition comprising a therapeutic amount of a compound of claim 1 in combination with a pharmaceutically acceptable carrier.

9. A composition according to claim 8 in unit dosage form wherein the compound of claim 1 is present in an amount of 10 milligrams to 200 milligrams.

* * * * *